(12) United States Patent
Novikau et al.

(10) Patent No.: US 10,234,667 B2
(45) Date of Patent: Mar. 19, 2019

(54) EVALUATION OF SIGNALS OF FLUORESCENCE SCANNING MICROSCOPY USING A CONFOCAL LASER SCANNING MICROSCOPE

(71) Applicants: Carl Zeiss Microscopy GmbH, Jena (DE); Carl Zeiss AG, Oberkochen (DE)

(72) Inventors: Yauheni Novikau, Jena (DE); Thomas Kalkbrenner, Jena (DE); Tiemo Anhut, Jena (DE); Daniel Schwedt, Weimar (DE); Matthias Wald, Jena (DE)

(73) Assignees: Carl Zeiss Microscopy GmbH, Jena (DE); Carl Zeiss AG, Oberkochen (DE)

(*) Notice: Subject to any disclaimer, the term of this patent is extended or adjusted under 35 U.S.C. 154(b) by 0 days.

(21) Appl. No.: 15/573,429

(22) PCT Filed: May 9, 2016

(86) PCT No.: PCT/DE2016/100207
§ 371 (c)(1),
(2) Date: Nov. 10, 2017

(87) PCT Pub. No.: WO2016/180403
PCT Pub. Date: Nov. 17, 2016

(65) Prior Publication Data
US 2018/0113292 A1 Apr. 26, 2018

(30) Foreign Application Priority Data

May 11, 2015 (DE) .................. 10 2015 107 367

(51) Int. Cl.
*G02B 21/00* (2006.01)
*G01N 21/64* (2006.01)

(52) U.S. Cl.
CPC ..... *G02B 21/0076* (2013.01); *G01N 21/6458* (2013.01); *G02B 21/006* (2013.01); *G02B 21/008* (2013.01); *G01N 21/6408* (2013.01)

(58) Field of Classification Search
CPC ............. G02B 21/0076; G02B 21/006; G01N 21/6458
See application file for complete search history.

(56) References Cited

U.S. PATENT DOCUMENTS

| | | |
|---|---|---|
| 5,239,178 A | 8/1993 | Derndinger et al. |
| 6,028,306 A | 2/2000 | Hayashi |

(Continued)

FOREIGN PATENT DOCUMENTS

| | | |
|---|---|---|
| DE | 103 56 416 A1 | 6/2005 |
| DE | 10 2014 002 328 A1 | 8/2015 |

(Continued)

OTHER PUBLICATIONS

Dertinger, T., et al.; "Fast, background-free, 3D super-resolution optical fluctuation imaging (SOFI)"; PNAS 2009; 106(52):22287-22292.

(Continued)

*Primary Examiner* — Hugh H Maupin
(74) *Attorney, Agent, or Firm* — Duane Morris LLP

(57) ABSTRACT

A method for evaluating signals of fluorescence scanning microscopy with simultaneous excitation and detection of fluorescence in different focal planes of a sample by means of confocal laser scanning microscopy. The invention evaluates signals of fluorescence scanning microscopy without the signal losses usually taking place with a confocal aperture, by coupling an illumination beam into a microscope observation beam path which images a measuring volume on a detector array arranged in the image plane, focusing the illumination beam which passes through a beam-forming (Continued)

phase mask for generating an elongated focus in the measuring volume, collecting and collimating fluorescent light generated in the measuring volume and routing it to diffractive optics which split the light beams into different diffraction orders and impress a different spherical phase on the light beams, imaging the different diffraction orders on detector regions of the detector array so that fluorescent light from focal planes at different depths of the measuring volume are associated with different diffraction orders, and associating the fluorescence signals on which crosstalk is superposed from different focal planes of the measuring volume with defined focal planes by means of correlation-based association based on distinguishable blinking behavior of fluorescing dyes.

21 Claims, 9 Drawing Sheets

(56) References Cited

U.S. PATENT DOCUMENTS

| | | |
|---|---|---|
| 2011/0226962 A1 | 9/2011 | Boudreau et al. |
| 2011/0300490 A1 | 12/2011 | Rachet et al. |
| 2013/0176622 A1 | 7/2013 | Abrahamsson et al. |
| 2016/0377850 A1 | 12/2016 | Anhut et al. |

FOREIGN PATENT DOCUMENTS

| | | |
|---|---|---|
| EP | 2 535 755 A1 | 12/2012 |
| WO | WO 2010/141608 A1 | 12/2010 |

OTHER PUBLICATIONS

Dertinger, Thomas, et al.; "Achieving increased resolution and more pixels with Superresolution Optical Fluctuation Imaging (SOFI)"; Optics Express 2010; 18(18):18875-18885.

Geissbuehler, Stefan, et al.; "Comparison between SOFI and STORM"; Biomedical Optics Express 2011; 2(3):408-420.

Blanchard, Paul M., et al.; "Simultaneous multiplane imaging with a distorted diffraction grating"; Applied Optics 1999; 38(32):6692-6699.

Makowski, M., et al.; "3D imaging with the Light Sword Optical Element and deconvolution of distance-dependent Point Spread Functions";Proc. of SPIE 2010;7746:00-1-00-8.

International Search Report dated Oct. 25, 2016.

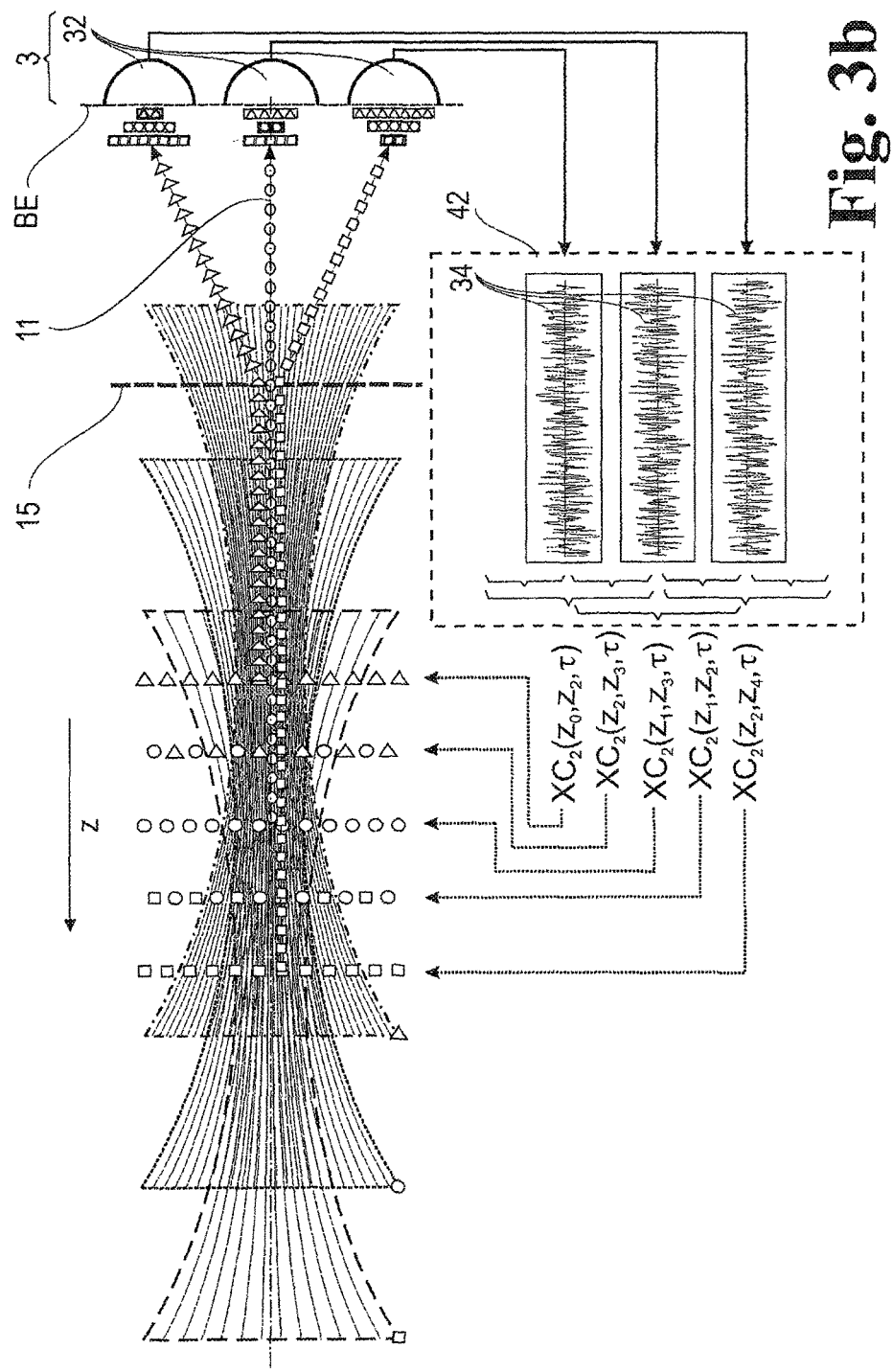

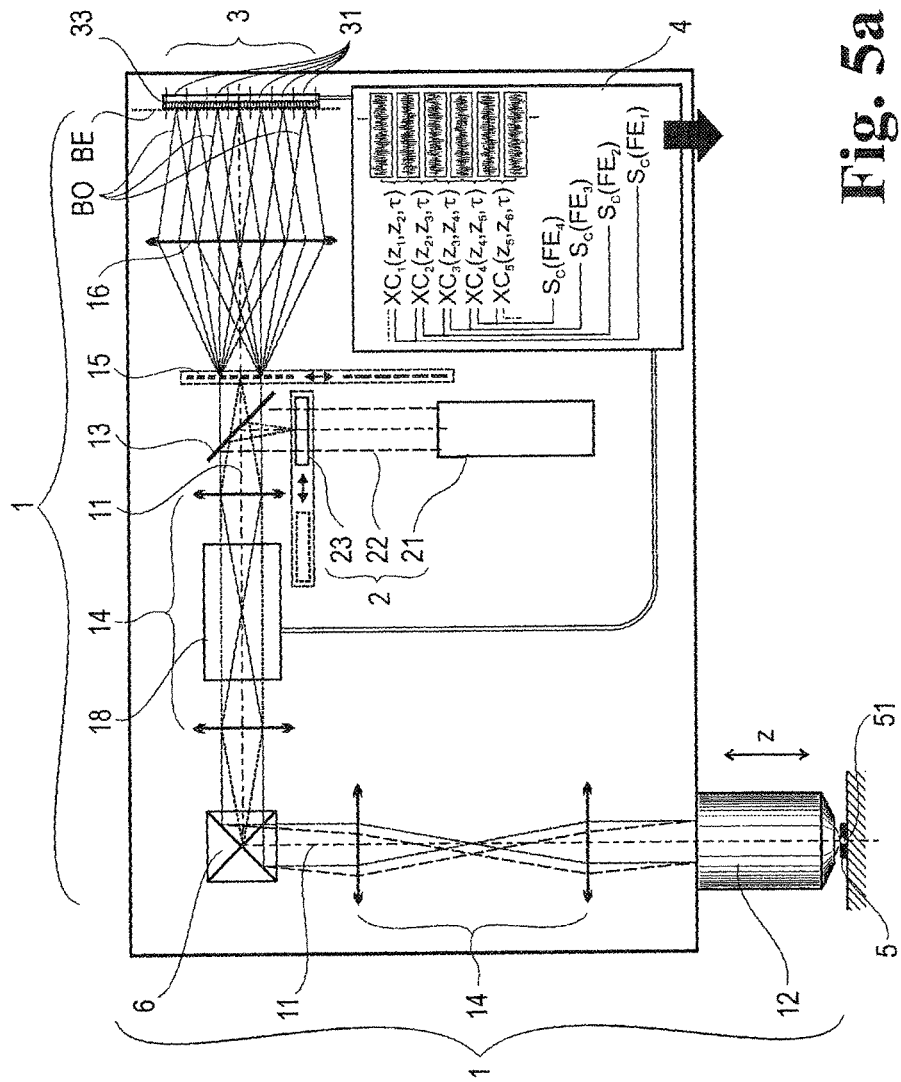

EVALUATION OF SIGNALS OF FLUORESCENCE SCANNING MICROSCOPY USING A CONFOCAL LASER SCANNING MICROSCOPE

RELATED APPLICATIONS

The present application is a U.S. National Stage application of International PCT Application No. PCT/DE2016/100207 filed on May 9, 2016 which claims priority benefit of German Application No. DE 10 2015 107 367.6 filed on May 11, 2015, the contents of each are incorporated by reference in their entirety.

FIELD OF THE INVENTION

The invention is directed to a method for the evaluation of signals of fluorescence scanning microscopy with simultaneous excitation and detection of fluorescence in different focal planes of a sample by means of confocal laser scanning microscopy, in particular for increasing efficiency of fluorescence scanning microscopy of thick samples, and to a confocal laser scanning microscope (LSM) with simultaneous fluorescence from different focal planes.

BACKGROUND OF THE INVENTION

Diverse attempts to improve the efficiency of the evaluation of fluorescent samples are known in prior-art confocal fluorescence scanning microscopy, e.g., in DE 197 02 753 A1.

Solutions in this regard diverge in their aims which are directed to:
  a) reducing measuring times in spite of scanning sequential image formation; and
  b) blur-free imaging through an optical section, i.e., separating out-of-focus fluorescent light from the usable focal signal through a confocal aperture.

Further, the known advantages of laser scanning microscopy (confocal microscopy) such as optical sectioning (suppression of out-of-focus signals) and high flexibility are accompanied by disadvantages and limitations:
  1) expenditure of time on sequential data acquisition;
  2) damage to sample (e.g., bleaching) through high intensity in the focus; and
  3) damage to sample (e.g., bleaching) through unused out-of-focus intensity.

The simplest solution for both of the above-mentioned aims a) and b), which would consist in increasing the intensity of the excitation light is not feasible as a singular approach because it is accompanied by an unwanted bleaching of the sample. Therefore, aim a) is chosen, e.g., through parallelization of measurements (multi-spot LSM, spinning disc), i.e., the simultaneous scanning of the sample with a plurality of foci which are then imaged through an own confocal pinhole or shared confocal pinhole onto a detector element or a detector array (camera, spinning disc). Accordingly, either the recording speed is increased or a larger surface area is scanned over the same time. Thus, at a given image capture rate, the second disadvantage can also be reduced in that the selected focal intensity can be reduced by the factor of parallelization. However, nothing changes with respect to the "waste" of out-of-focus photons (third disadvantage). This last aspect—apart from the unwanted stress on the sample—represents a fundamental limitation of the confocal method in that many planes of the sample are illuminated but are not evaluated although the integrated excitation output is the same in every plane.

Possibilities for reducing stressing of samples through parallelized image capture are described, for example, in U.S. Pat. No. 5,239,178 or U.S. Pat. No. 6,028,306 with N separate measuring volumes (referred to as measuring points for the sake of simplicity) which are illuminated and measured simultaneously in the focal plane. The sample can be measured with less intensity per illumination beam at the same time at N points. The illumination intensity is reduced by the factor 1/N and the pixel dwell time is lengthened by the factor N so that the frame rate is identical to, and the SNR is comparable to, the raster scanned recording by means of an individual measuring volume. While the energy dose entering the sample is the same, it is spatially distributed such that the peak intensity which is harmful to the sample can be reduced per illumination point.

An image capture with the same advantages which is parallel in many respects can also be accomplished by means of a rotating Nipkow disc or with linear scanning.

An alternative kind of parallelized image capture consists in simultaneous imaging of measuring points from different image planes, also known as axial multifocal imaging.

For example, it is known from DE 103 56 416 A1 to achieve a simultaneous imaging of a plurality of separate measuring volumes located along the optical axis of the microscope objective based on monochromatic confocal microscopy by means of an optically decentered diffractive optical element (DOE, e.g., phase grating) and collector optics in that the different curvature of wavefronts originating from sample planes at different distances from one another is used to distribute them through the DOE in different diffraction orders and to image them in an individual plane, preferably the confocal aperture plane. All of the wavelengths except that of the illumination light are then discriminated with a confocal aperture, so this multifocal imaging variant is not suitable for florescence measurements (because of Stokes shift and the spectral bandwidth of the florescence emission).

Systems for multifocal imaging in wide-field microscopy work on the same principle as described, for example, by: Blanchard et al. (1999), "Simultaneous multiplane imaging with a distorted diffraction grating", *Appl. Opt.* 38 (32): 6692-6699; Dalgarno et al. (2010), "Multiplane imaging and three-dimensional nanoscale particle tracking in biological microscopy", *Optics Express* 18 (2): 877-884; and Abrahamsson et al. (2013), "Fast multicolor 3D imaging using aberration-corrected multifocus microscopy", *Nature Methods* 10 (1): 60-63.

Prior-art fluorescence microscopy also includes methods of fluorescence correlation analysis of which SOFI (Superresolution Optical Fluctuation Imaging) is mentioned in particular. This method is described in the following publications:
  WO 2010/141608 A1;
  Dertinger, T.; Colyer, R.; Iyer G.; Weiss, S.; Enderlein, J. (2009). "Fast, background-free, 3D superresolution optical fluctuation imaging (SOFI)". In *PNAS* 106 (52): 22287-92;
  Dertinger, T.; Colyer, R.; Vogel, R.; Enderlein, J.; Weiss, S. (2010). "Achieving increased resolution and more pixels with Superresolution Optical Fluctuation Imaging (SOFI)", *Optics Express* 18 (18): 18875-84;
  Geissbuehler, S.; Dellagiacoma, C.; Lasser, T. (2011). "Comparison between SOFI and STORM", *Biomed. Opt. Express* 2 (3): 408-420.

In wide-field fluorescence detection (direct imaging of a plane of the sample by means of a camera), fluctuations of fluorescence emitters are evaluated by means of SOFI with a defined temporal correlation in order to obtain a fluorescence imaging with increased resolution over the diffraction limit. The degree to which resolution is increased depends on the order of the correlation function that can be evaluated. The latter in turn is heavily dependent upon the fluctuating system and signal quality. Necessary prerequisites for the application of SOFI are:

- the fluorescing system (molecule) must have at least two distinguishable fluorescence states (e.g., ON/OFF);
- different emitters (molecules) must change, or "blink", independently from one another and stochastically between these states; and
- the switching between states must be temporally detectable by an image sensor (area detector).

The first two prerequisites are met in principle for a large number of (basically all) fluorescing molecules (organic dyes and proteins); the OFF state can be, for example, a triplet state (according to FIG. 1 in Widengren, J. (2010). "Fluorescence-based transient state monitoring for biomolecular spectroscopy and imaging", *J. R. Soc. Interface* 7 (49): 1135-1144) or other non-radiatively decaying state. It is also conceivable that radiative relaxation pathways can be discriminated via the wavelength. However, to date, SOFI has only been able to be demonstrated for specific fluorescence systems because the time scales within which the triplet OFF state occurs are much too short even for the fastest available continuous-operation area detectors (CMOS, CCD). The corresponding times can be read, for example, off a typical measurement curve of a Jablonski diagram (see FIG. 1 in J. Widengren, op. cit.). A three-state model of a fluorophore and an FCS (Fluorescence Correlation Spectroscopy) are shown in the latter as (a) and (c), respectively, where the lifetime of the triplet state $t_T$ is in the microsecond range.

Examples of specific systems which are detectable, however, are quantum dots (Dertinger et al. [2009] *PNAS*) which exhibit blinking on almost all time scales and dSTORM systems (Geissbühler et al. [2011] *Opt Express*) in which the blinking behavior of the emitters is rendered in time intervals that can be detected by cameras through the adaptation of the chemical environment and of the excitation conditions that is known from the dSTORM method. Therefore, SOFI and dSTORM methods are not suitable for the broad application of common fluorescent dyes.

Hereinafter, the word "dyes" will be used for both endogenous (autofluorescence) and exogenous fluorescent dyes as well as for fluorescing proteins which exhibit the temporal behavior required for the method.

Based on a fluorescence scanning microscope in the form of a multi-confocal laser scanning microscope, e.g., according to the not-prior-published DE 10 2014 002 328, with first diffractive optics arranged in the observation beam path between a beam combiner and the image plane for splitting light beams into beam bundles of different diffraction orders which have different spherical phases relative to one another, with second diffractive optics for compensation of chromatic aberrations generated through the first diffractive optics, and with collector optics for focusing the split beam bundles in the image plane so that a series of different disjoint measuring volumes arranged along the optical axis of the microscope objective is imaged on the object side in the image plane simultaneously (along the different diffraction orders of the diffractive optics), the problem remains in multi-confocal detection with the laser scanning microscope described above that confocal detection would have to be carried out again on every sensor in order to acquire an image with optical depth resolution (known as sectioning). In this respect, it does not matter whether the light passes through a physical pinhole or is filtered confocally through utilization of the pixel-per-depth plane separation on the sensor. For this reason, however, it is to be expected as disadvantageous that the detection is in no way more light-efficient than in the sequential mode of sectioning with confocal fluorescence microscope.

The "light losses" can be explained by the fact that when light is split with chirped gratings, light also proceeds in diffraction orders which image "out-of-focus". An effect of this kind equates to the effect when using neutral splitters as described, for example, by Dalgarno et al. (2010) *Optics Express* 18 (2): 881, FIG. 2. In this case, a plane is sharply imaged with only a portion of the light, which is given by the splitting ratio of the beamsplitter, and the input intensity in the splitting ratio is consequently diminished. The splitting of the light with chirped gratings acts in exactly the same way as if observing with N neutral splitters in N different planes. While this makes the multi-(con)focal arrangement faster (parallelization in Z direction), the light arriving out-of-focus at the respective pinhole from other planes would be lost with confocal detection on a sensor element. But the goal of a parallelized arrangement should be to evaluate all of the light of the emitters from the respective conjugate sensor planes (i.e., from those planes of the sample that are sharply imaged by the respective sensor element).

If there were only one luminescent particle present within the excitation and detection PSFs in a so-called elongated focus range, the signal could be associated with the correct location in the sample by simultaneous non-confocal measurement of all of the planes with a pixelated sensor.

In this way, a "quasi-confocal image" would be achieved with increased efficiency, this image being generated in a manner basically corresponding to the procedure in a three-dimensional deconvolution in which the measured 3D light distribution is distributed among different sensors. However, in real measurements, an individual luminescent particle is virtually never assumed so that, in real samples, the signals from planes which are offset in the direction of the optical axis are superposed on one another on the sensor segments and, in case of a sample structure which is unknown a priori, can no longer be unequivocally associated with the planes because there is substantial crosstalk of signals from "blurrily imaged" planes on the detectors for diffraction orders separated through the DOE system owing to the absence of a confocal discrimination of signals from different planes. Moreover, the PSF is normally symmetrical so that, without further information, the portions which are defocused "up" and "down" could not be differentiated.

OBJECTS OF THE INVENTION

Therefore, it is an object of the invention to provide a possibility for evaluating signals of fluorescence scanning microscopy with a high resolution and depth discrimination (known as sectioning) comparable to that of a confocal microscope without the loss of a large number of fluorescence photons at the confocal aperture (pinhole) when using a confocal fluorescence scanning microscope (e.g., according to DE 10 2014 002 328) in which, by means of diffractive optics for splitting into bundles, there is impressed on the bundles in every diffraction order a spherical phase differing from the other diffraction orders, the wavefronts from different focal planes, which wavefronts are accordingly differently curved, are split into different diffraction orders and are detected exclusively on the illumination wavelength. In other words, signals arriving (axially) in parallel in Z direction from blurrily imaged planes are not filtered out through (real or virtual) confocal pinholes but rather contribute to the wanted signal of the sharply (confocally) imaged plane.

In a method for evaluating signals of fluorescence scanning microscopy with simultaneous excitation and detection of fluorescence in different focal planes of a sample by means of confocal laser scanning microscopy, the above-stated object is met according to the invention through the following steps:

at least one illumination beam is coupled by means of a beam combiner into a microscope observation beam path which is defined by a measuring volume of the sample up to an image plane and which has, along an optical axis, a microscope objective, the beam combiner for coupling in the illumination beam, and a detector array arranged in the image plane, the illumination beam is focused with the microscope objective in the measuring volume, wherein the illumination beam passes through a beam-forming phase mask in an illumination pupil for generating an elongated focus, fluorescent light generated in the measuring volume is collected and collimated by means of the microscope objective, and resulting light beams are routed to diffractive optics arranged between the beam combiner and the image plane, the light beams generated in the measuring volume are split into beam bundles of different diffraction orders by means of the diffractive optics and the different diffraction orders are imaged on separate detector regions of the detector array by means of detection optics, wherein the diffractive optics impress upon the light beams of every diffraction order a spherical phase differing from the other diffraction orders so that fluorescent light from focal planes of different depths of the measuring volume is associated with different diffraction orders and is deflected without confocal discrimination to the separate detector regions by which fluorescent light from associated focal planes of the measuring volume and fluorescence crosstalk from blurrily imaged adjacent focal planes of the measuring volume are converted into electronic fluorescence signals, and the fluorescence signals which originate from different focal planes of the measuring volume and on which crosstalk is superposed along the diffraction orders are associated with focal planes defined in the measuring volume by means of correlation-based association of the fluorescence signals based on distinguishable blinking behavior of fluorescing dyes in the measuring volume.

The association of the fluorescence signal with the focal planes is advantageously carried out through second-order cross-correlation of signal sequences of two detector regions of neighboring diffraction orders.

The cross-correlation of the signal sequences is advisably carried out over a time period adapted to the fluorescence blinking of the dyes.

Dyes with a duration of an OFF state of fluorescence blinking between 0.1 µs and 500 µs, preferably between 1 and 100 µs, particularly between 5 and 50 µm, are advantageously used.

The correlation of signal sequences is carried out over a quantity of frames corresponding to ten times to one thousand times an OFF state of the fluorescence blinking. It is advisably carried out over a quantity of frames twenty to fifty times the OFF state of the fluorescence blinking. A 3D deconvolution can be carried out in addition to the cross-correlation.

The measuring volume is advantageously illuminated with an elongated focus in order to further spread out a given number of focal planes in the measuring volume depth.

In this regard, it turns out to be advantageous that the spreading out of the focal planes and an increased resolution in the measuring volume depth can be selectively adjusted in that the elongated focus is adjusted by means of a zoom objective between the sample and the diffractive optics.

The elongated focus can advantageously be adjusted by underfilling the entrance pupil of the microscope objective. In this regard, an additional correlation of fluorescence signals scanned in lateral planes of the sample with increased lateral resolution is achieved to supplement the correlation of fluorescence signals in depth with elongated focus which is expanded by underfilling the entrance pupil of the microscope objective.

In addition to the correlation in depth, an additional correlation can advisably be carried out for fluorescence signals scanned in lateral planes of the sample.

Further, in a confocal fluorescence scanning microscope with an optical system which defines a microscope observation beam path from a measuring volume to an image plane and has a microscope objective, a beam combiner for coupling an illumination system, and an aperture arranged in the image plane, the above-stated object is met in that the optical system comprises diffractive optics in the observation beam path between the beam combiner and the image plane for splitting light beams into beam bundles along different diffraction orders, wherein there is impressed on the beam bundles of every diffraction order a spherical phase which differs from the other diffraction orders, and detection optics for focusing the split beam bundles on separate detector regions of the detector array, in that the detector array has a number of separately readable detector regions which corresponds to the quantity of diffraction orders so that fluorescent light arriving from a defined focal plane in the associated diffraction order and crosstalk fluorescent light from neighboring focal planes in the same diffraction order can be received in the detector regions, and in that there is arranged downstream of the outputs of the detector regions an evaluating and controlling unit for associating the fluorescence signals which originate from the same focal planes but which are received by different detector regions, which evaluating and controlling unit comprises means for correlating different signal components and for associating correlating signal components with exactly one focal plane in each instance based on distinguishable blinking behavior of fluorescing dyes in the measuring volume.

The diffractive optics are advantageously configured as a chirped grating.

It has proven especially advantageous that a spherical phase is impressed upon the light beams of every diffraction order through the diffractive optics, which spherical phase differs from the other diffraction orders by an integral multiple in each instance.

Zoom optics for underfilling the entrance pupil of the microscope objective can advisably be provided as means for forming an elongated focus. The laser for exciting the sample has means for generating a Bessel beam or other non-diffractive beam as particularly preferred means for forming an elongated focus.

In both cases, it proves advantageous that zoom optics for underfilling the entrance pupil of the microscope objective are provided in order to further spread apart the distances of the focal planes.

Additionally, means can be provided for lateral scanning and linking means can be provided for generating a stack of laterally two-dimensionally scanned frames in different focal planes comprising fluorescence signals which are captured pixel by pixel and by cross-correlation of signal components associated with the various focal planes.

In this respect, a cross-correlator for analyzing fluorescence signals from respective vertically adjacent focal planes and laterally adjacent pixels of the frames is advantageously provided in the evaluating and controlling unit for associating signal components with exactly one focal plane.

In a further arrangement, a processor unit for 3D deconvolution of fluorescence signals from respective vertically adjacent focal planes and laterally adjacent pixels of the frame is provided in the evaluating and controlling unit for associating signal components with exactly one focal plane.

The invention is based on the consideration that an appreciably higher photon efficiency (namely, ratio of detected fluorescence photons to radiated photons) of the signals of fluorescence scanning microscopy using a confocal laser scanning microscope (CLSM) can only be achieved through further parallelization of detection and evaluation because, in any case, the excitation power may not be increased indiscriminately if photodamage of the samples is to be substantially avoided. In confocal fluorescence scanning microscopy, however, a further parallelization of signal recordings is possible only in direction of the optical axis when the signal components which originate from "blurry" focal planes and which were previously eliminated through confocal discrimination are now permitted for signal formation on the detector. Of course, this entails the problem that the signals from different planes which are offset in direction of the optical axis are superposed with one another on the detector segments and can no longer be unequivocally associated with the planes without knowledge of the sample structure.

The intended goals of: (a) reducing photodamage of samples; and (b) reducing capture times for given 3D volumes (i.e., for thick samples), can only be realized in that the radiated output is virtually constant in all focal planes such that the fluorescence generated therefrom need only be evaluated simultaneously in all focal planes. This is in turn only possible when signal components which do not originate from the primary focal plane are admitted for signal capture and are subsequently correctly associated with the focal planes. This problem is solved according to the invention through correlation of the signals from the detector regions. Since different emitters blink (i.e., have different fluctuations in the emission characteristic) independently from one another stochastically, it is possible to associate correlating fluorescence signals of adjacent detector regions with a determined emitter. This is the case for virtually all emitters, although the mechanisms and, therefore, the time scales of the fluctuations differ for different planes, so that the fluorescence emitters in the different planes have an uncorrelated emission behavior in direction of the optical axis by means of which they can be separated subsequently.

BRIEF DESCRIPTION OF THE DRAWINGS

The invention will be described more fully in the following with reference to embodiment examples and drawings. The drawings show:

FIG. 3b is a schematic diagram as in FIG. 3a with crosstalking captured signals cross-correlated subsequently according to the invention for generating efficient pixels separated in Z direction and additional pixels from intermediate planes which result from cross-correlation of fluorescence signals of adjacent detectors;

FIG. 5a is a schematic diagram showing the beam path of a multifocal LSM according to the invention with subsequent correlation analysis for five diffraction orders, assumed for the sake of simplicity, with crosstalking fluorescence signals as are shown schematically in FIG. 3 for three diffraction orders;

FIG. 5b is a schematic diagram of a CLSM with multiconfocal correlation analysis, according to the invention, for five diffraction orders, assumed for the sake of simplicity, with crosstalking fluorescence signals as shown in FIG. 5a.

DESCRIPTION OF THE EMBODIMENTS

Figure 1:
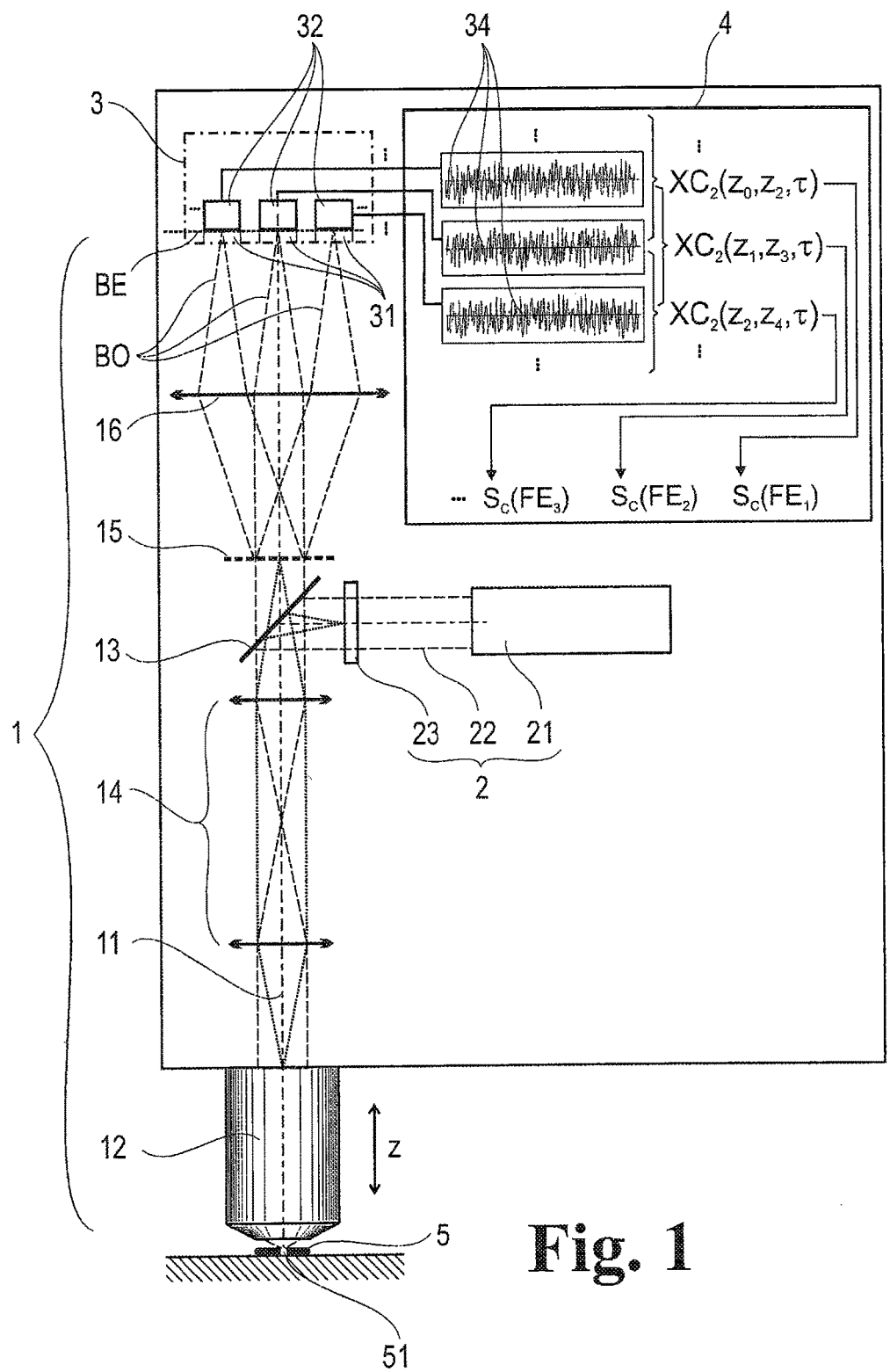
FIG. 1 is a schematic diagram of the measuring method according to the invention.

The basic flow of the method which can be perceived based on a confocal laser scanning microscope shown schematically in FIG. 1 and which has as subject matter the evaluation of signals of fluorescence scanning microscopy with simultaneous excitation and detection of fluorescence in different focal planes FE of a sample 5 includes the following steps.

At least one illumination beam 22 is coupled by means of a beam combiner 12 into a microscope observation beam path 1 which is defined by a measuring volume 51 of the sample 5 up to an image plane BE and which has, along an optical axis 11, a microscope objective 12, the beam combiner 13 and a detector unit 3 arranged in the image plane BE.

Next, the illumination beam 22 is focused with the microscope objective 12 in the measuring volume 51, wherein the illumination beam 22 passes through a beam-forming phase mask 23 in an illumination pupil for generating an elongated focus.

Fluorescent light generated in the measuring volume 51 is collected and collimated by means of the microscope objective 12, and resulting light beams are routed to diffractive optics 15 arranged between the beam combiner 13 and the image plane BE.

The light beams generated in the measuring volume 51 are split into beam bundles of different diffraction orders BO by means of the diffractive optics 15 and the different diffraction orders BO are imaged on separate detector regions 31 of the detector array 3 by means of detection optics 8, wherein the diffractive optics 15 impress upon the light beams of every diffraction order BO a spherical phase differing from the other diffraction orders BO so that fluorescent light from focal planes FE of different depths of the measuring volume 51 is associated with different diffraction orders BO and is deflected without confocal discrimination to the separate detector regions 31 by which fluorescent light from associated focal planes FE of the measuring volume 51 and fluorescence crosstalk from blurrily imaged adjacent focal planes FE of the measuring volume 51 are converted into electronic fluorescence signals 34.

And, the fluorescence signals 34 which originate from different focal planes FE of the measuring volume 51 and on which crosstalk is superposed along the diffraction orders BO are associated with focal planes FE defined in the measuring volume 51 by means of correlation-based association of the fluorescence signals 34 based on distinguishable blinking behavior of fluorescing dyes in the measuring volume 51.

The aim of the method is not primarily to generate a superresolved image but rather, through subsequent pixel correlations, to make use of the separation and association of fluorescence signals of different fluorescing emitters, which are arranged in space (i.e., in the sample volume depth) and which are superposed multifocally in a multifocal LSM as a result of signal detection which is consciously not strictly confocally discriminated, for increasing photon efficiency. Therefore, this method may be referred to in short as CPI (correlated pixel imaging). The background to why this CPI approach works at all will be discussed in detail in the following paragraph.

An axially elongated focus region or, for short, elongated focus, will be referred to numerous times in the following. By this is meant that this focus can be lengthened approximately twofold to tenfold compared to a "normal" focus which is usually "expanded" in Z direction over 0.5 μm to 150 μm as extended intensity distribution with a laser. The length of this elongated focus depends on the required depth of the Z scan or on the thickness of the sample 5 to be examined. An elongated focus of this kind can be generated—according to FIG. 1—through a phase mask 23 within the illumination pupil and during detection by means of diffractive optics 15 (as a specific DOE or diffractive optical element).

If there were only one luminescent particle in a thick sample 5 in an elongated focus, the signal component from every plane could be associated with the appropriate focus point and, therefore, with the location in the sample and "added" to the latter by simultaneous non-confocal measurement of all of the planes with a pixelated sensor (matrix detector). Accordingly, a "quasi-confocal image" is obtained which has a higher photon efficiency than could ever be achieved by an LSM with strictly confocal detection. This procedure basically corresponds to a three-dimensional deconvolution, and the measured 3D light distribution is distributed to different sensors. However, this is virtually never the case in real measurements because, with real samples 5, the signals from planes which are offset in direction of the optical axis are superposed on one another on the detector regions 31 and can no longer be unequivocally associated with focal planes FE with a sample structure 52 which is unknown a priori (see example in FIG. 4a).

Figure 2:
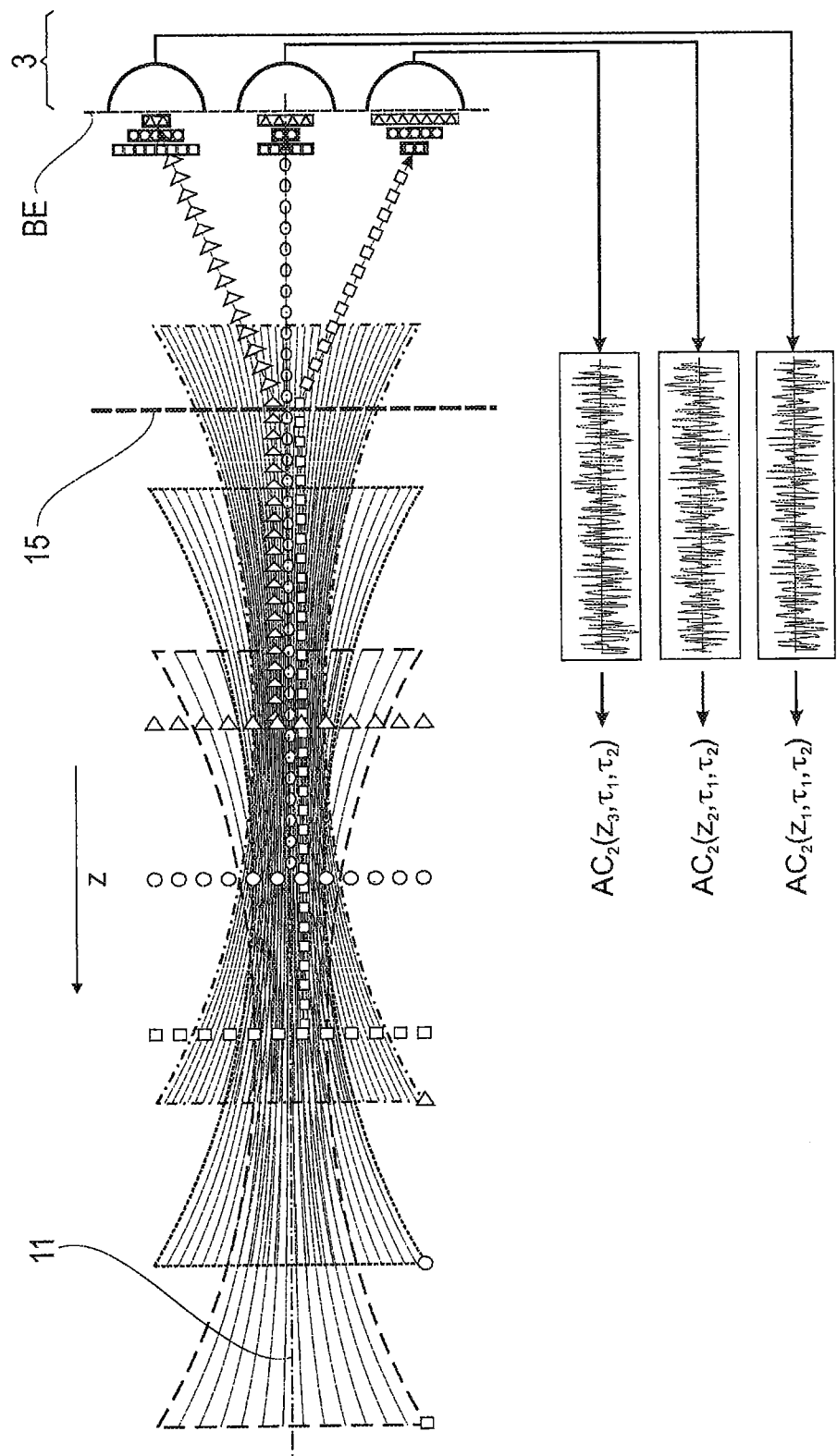
FIG. 2 is a schematic diagram of a confocal laser scanning microscope (with DOE only shown symbolically and pinhole removed from the confocal plane) for fluorescence scanning microscopy in which detection is carried out simultaneously in three planes (dashed lines), there is crosstalk between associated detector elements because confocal detection is dispensed with, and in which the association of the respective detection PSF is represented by different fill patterns.

The real world case for signal components is shown schematically in FIG. 2 for three focal planes FE which are offset in Z direction. Due to the absence of a confocal discrimination of the optical fluorescence signals from the different focal planes FE, there is considerable crosstalk of signals from "blurrily imaged" focal planes FE on the detector regions 31 allocated for the separated diffraction orders BO. In this case, represented in a simplified manner, the diffractive optics 15 which are only indicated schematically generate a simultaneous detection from three focal planes FE identified by different symbols (triangle, circle, square), the associated detector regions 31 which can be individual detectors 32 or segments of a detector array 33 (shown only in FIG. 3C), and the respective detection PSFs. In this regard, the association of the fluorescent light in the detector unit 3 with the three selected focal planes FE is symbolized in FIG. 2 by dashed lines of different thickness and an additional margin symbol. The bars in front of the individual detectors (individual detectors 32 in FIG. 2) symbolize the signal components from the respective focal planes FE. However, since the latter are detected by the individual detector 32 only in sum, there is no possibility of associating the components with the focal planes FE.

The detector signal of each individual detector 32 comprises an intensity signal over time. This time series is autocorrelated with a fixed delay (time lag) τ in order to suppress out-of-focus contributions. The autocorrelation signal is defined as follows:

$$AC_2(n, \tau) = \frac{\langle (I(n, t) - \langle I(n, t)\rangle) * (I(n, t+\tau) - \langle I(n, t)\rangle)\rangle}{\langle (I(n, t))\rangle^2} = \quad (1)$$

$$\langle \delta I(n, t+\tau) * \delta I(n, t)\rangle_t,$$

where AC is the autocorrelation or autocumulant and n is the XY plane in the respective focal plane FE.

This means that the time signal is multiplied by itself after a time lag according to the above equation. A number of these measurements can then be statistically averaged (so-called ensemble averaging, which can be carried out as time averaging based on the present processes). The correlation amplitude is used as pixel signal (or pixel value). Alternatively, the autocorrelation of the time series can also be carried out over a plurality of (many) τ; the correlation amplitudes are then integrated (summed) over this time range. Ideally, τ≠0 is not taken into account because the shot noise would then be suppressed.

However, an increase in photon efficiency would still not be possible in the signal processing according to FIG. 2. Crosstalking signal components are completely lost.

However, this problem can be solved through correlation of the fluorescence signals 34 from neighboring detector regions 31 when the fluorescence emitters have an uncorrelated emission behavior in the different focal planes FE. In the event that different emitters "blink" (i.e., have different fluctuations in the emission characteristic) stochastically independently from one another, it is possible to associate correlating fluorescence signals 34 with a determined emitter. However, stochastic blinking exists for virtually all emitters, and the mechanisms and, therefore, the time scales of the fluctuations differ for different emitters, and this property can be utilized for distinguishing between the different focal planes FE.

Figure 3A:
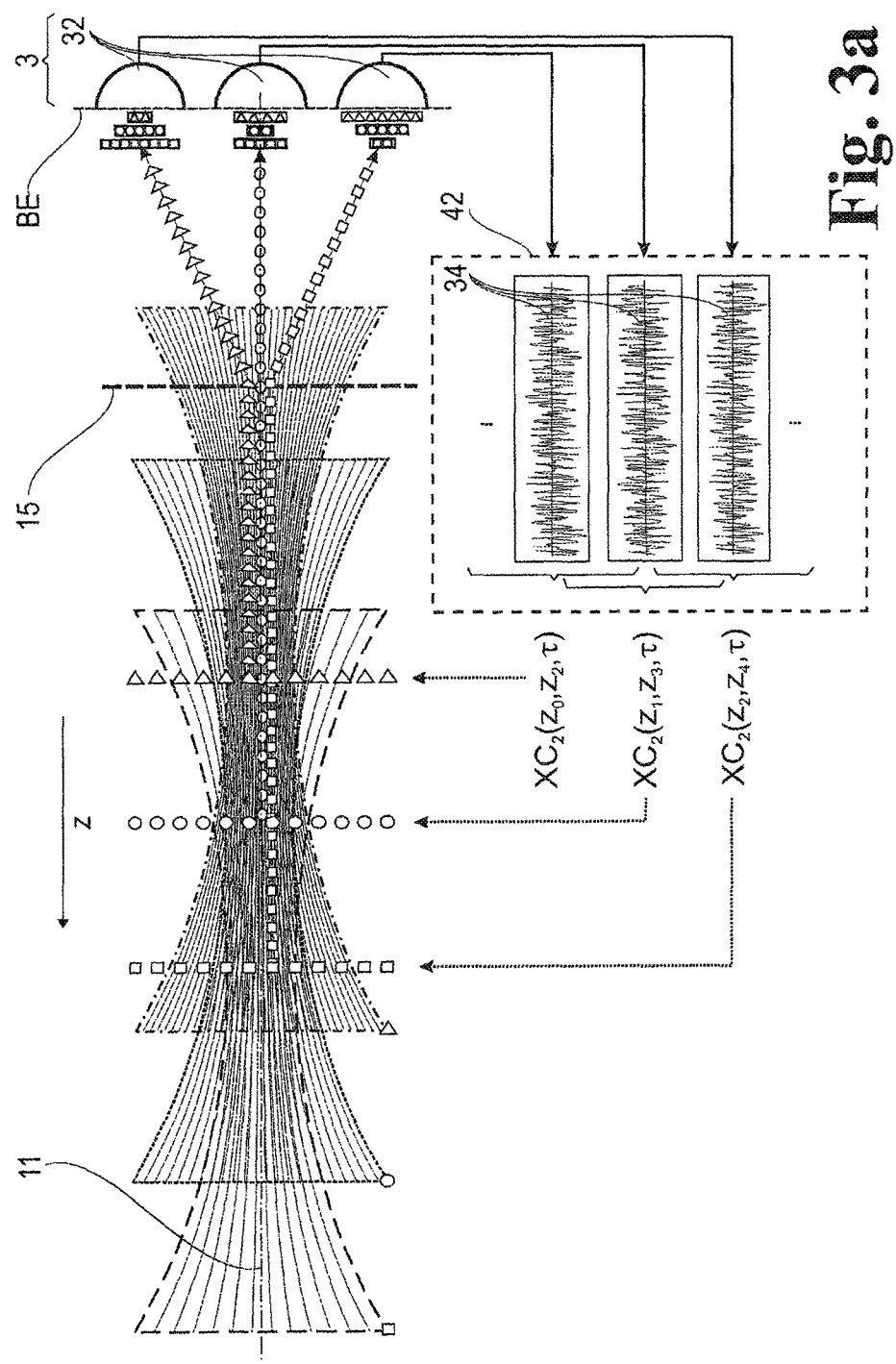
FIG. 3a is a schematic diagram as in FIG. 2 with crosstalking captured signals cross-correlated subsequently according to the invention for generating efficient pixels separated in Z direction.
Figure 3C:
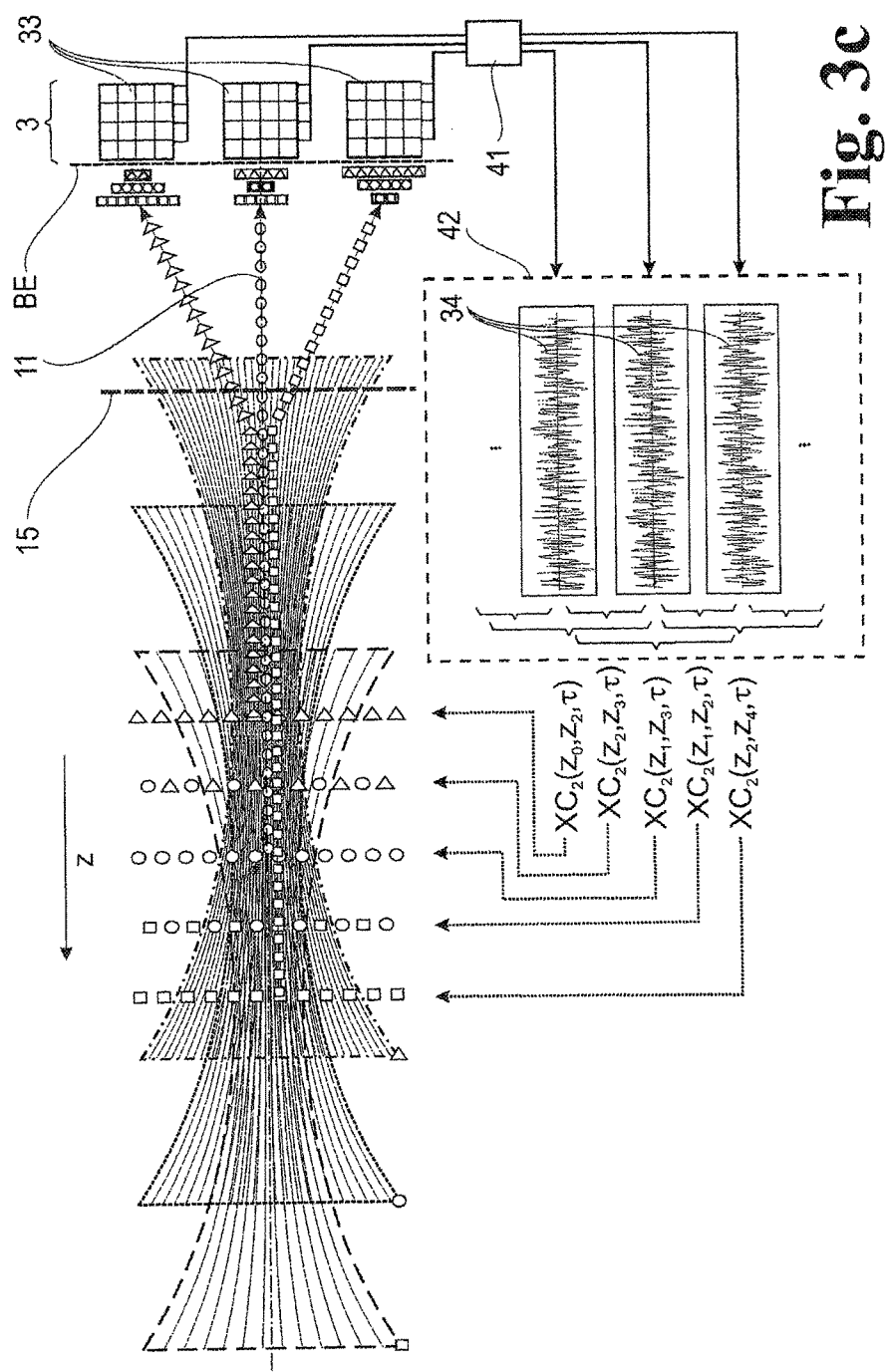
FIG. 3c is a schematic diagram as in FIG. 3b with subsequent cross-correlation according to the invention for generating efficient pixels separated in Z direction and intermediate pixels, but in which the crosstalking signals are acquired by multi-element sensors.

FIG. 3a shows the diagram from FIG. 2, but with a cross-correlation of the fluorescence signals 34 for sorting out the correct signal components on the real pixel positions in Z direction. In order to solve the challenging sensor technology problem of resolving the different time scales of the fluorescence emitters at all, i.e., their stochastic "blinking", a further advantage of the detection method, namely, the quasi-confocal acquisition of measurement values, is made use of.

The measuring method according to the invention works quasi-confocally and does not rely on the use of high-resolution cameras, but rather can resort to much faster detectors (SPAD arrays, PMT arrays, fiber-coupled detector arrangements, cameras with small programmable pixel regions which can be read out quickly) owing to the limited number of required detector regions 31. Accordingly, the method is not limited to specific emission systems such as quantum dots and dSTORM dyes. On the contrary, virtually all standard dyes having a triplet lifetime in the range of 1-100 µs can now also be used with the method according to the invention.

Since this also involves a "point"-scanning method (where "point" refers here to a position in a lateral X-Y raster and, strictly speaking, this would be a line-scanning method in which the "scan line" extends in Z direction"), it is even advantageous when this time scale is short so as to acquire the blinking cycles needed for correlation with the shortest possible pixel dwell time.

As a result of the fast individual detectors and small multi-element detectors (with particularly short readout times) which are used for the present method, the above-mentioned timing of the triplet lifetime of less than 100 µm (particularly 1-100 µm) is made available and, therefore, a large class of dyes is made accessible for the present method. The time scale for "point scanning" (pixel dwell time) is set at <1 ms, where the 0.5-500 µs range is considered advantageous for the use of multivalent dyes. "Fast blinking" dyes (with characteristic blinking times of $\tau \leq 10$ µs) are preferably used to achieve pixel dwell times between 5 µs and 50 µs and, therefore, to allow lateral area scanning, i.e., to record a stack of, e.g., 25 frames with 256×256 pixels in a few seconds, e.g., 1-20 s.

In the present method, the cross-correlation or cross-cumulant is formed, and the following variants are possible:
1) plane n+1 is cross-correlated with plane n−1 to determine existing contributions to plane n, shown is FIG. 3a;
2) plane n is correlated with plane n+1 to generate an intermediate plane n+½ (not shown separately); and
3) the cross-correlation of planes n+1 and n−1 and planes n and n+1 give the total result from FIG. 3b.

Broadly speaking:

$$XC_2(n_i, n_j, \tau) = A_{ij} \Sigma_{i,j} \langle \delta I(n_i, t+\tau) * \delta I(n_j, t) \rangle_t \quad (2)$$

where XC is the cross-correlation or cross-cumulant, $n_i$ is plane i and $A_{ij}$ is a weighting factor.

For i=j (corresponds to autocorrelation as described referring to FIG. 2), it is again true that the shot noise is suppressed only for $\tau \neq 0$; for i≠j this is also true in case $\tau = 0$ because the shot noise of neighboring planes/detector elements is uncorrelated. Accordingly, $\tau = 0$ also—or even only $\tau = 0$—can be evaluated during the cross-correlation. The latter can facilitate a fast "online" calculation of the pixel values (FPGA, also analog-electronically in principle).

As in the preceding, this correlation can be carried out for a fixed time lag $\tau$ or for many $\tau$. The correlation amplitude or the sum of correlation amplitudes is again read out as pixel information. Accordingly, the resulting image does not show the fluorescence labeling of the sample directly, but rather shows its spatially-resolved brightness and the correlation strength of the emitters in the sample.

When cross-correlating across the planes, a weighting of the contributions from the planes must still be carried out. For the preferred case in this instance, where equidistant planes are correlated, the weighting is simply carried out via the distance ratios, i.e., for the case of neighboring planes which is also preferred in this instance, the weighting factor is simplified to ½.

The usefulness of the invention consists in an appreciably higher photon efficiency (ratio of detected fluorescent photons to radiated photons) and, as a result of this, reduced capture times for given 3D volumes as well as reduced photodamage and reduced bleaching.

In the 3D capture of fluorescence, scanning steps in lateral direction which are preferably carried out in the Cartesian raster of the two coordinate directions X and Y are added to the Z line scan realized according to the invention. During the lateral scanning in a rectangular X-Y raster, the Z line scan according to the invention is carried out in every scan position so that, given an organized stacking of the lateral scan steps with the associated focal plane recordings in Z direction, a 3D stack of pixel data of (X, Y) frames located one above the other in Z direction results. Here, the term "frame" means the conventional Cartesian 2D pixel configuration with (lateral) X-Y scanning. A frame of this kind is acquired in multi-(con)focal 3D scanning as pixel field simultaneously for each individual focal plane FE in n planes and is stored as a stack.

Expansion to Detectors with Subpixel Structure

Up to this point, detectors 3 have been regarded as arrays of detectors, of which a detector region 31 is normally interpreted as an individual sensor element and is associated with a focal plane FE.

However, in case of fast detector arrays with many pixels or fast camera systems it is also possible to associate a region of the detector array having a plurality of pixels with each focal plane FE. The signals of these pixels from the detector region 31 of the array that is associated with a focal plane FE can be summed so that the detector region 31 behaves like a point detector and all of the preceding considerations apply in an analogous manner. This is the case shown in FIG. 3c, wherein the evaluation is carried out in basically the same manner as in FIG. 3b and it need only be distinguished whether the detector arrays 33 are combined, averaged or further processed as individual pixels.

If sufficiently many pixels are available per focal plane FE, the PSF of every focal plane FE can also be laterally resolved. As has been the case heretofore, the contributions of the different focal planes FE must be separated by correlation (XC or AC). Subsequently, however, the additional information of the lateral intensity distribution in every focal plane FE can also be utilized. This can be carried out through local deconvolution or through local model-based adaptation of a local fluorescence distribution in the measured 3D intensity distribution, where "measured" means the detector signals already associated by correlation, which has already been described.

The signal quality and resolution of the lateral detector signal per focal plane can be additionally increased through lateral cross-correlation of the pixels within a focal plane FE.

Up to this point, a correlation of the second order has always been assumed. With higher-order correlations, lower-order mixed terms occur. These mixed terms are not wanted in measurements in which the central moments are to be determined. Consequently, cumulants are defined such that for a cumulant of a determined order the contributions of the lower-order moments disappear, see, e.g., Biman Das and Nicolas Lyga (2001). "Cumulant-like cross-correlation functions to determine temporal behavior of two signals", *Bulgarian Journal of Physics* 28 (3/4): 120-127. For the second order, which is particularly important for the present invention, and for the third order, the cumulant is identical to the correlation function. This distinction only becomes important for higher orders.

Figure 4:
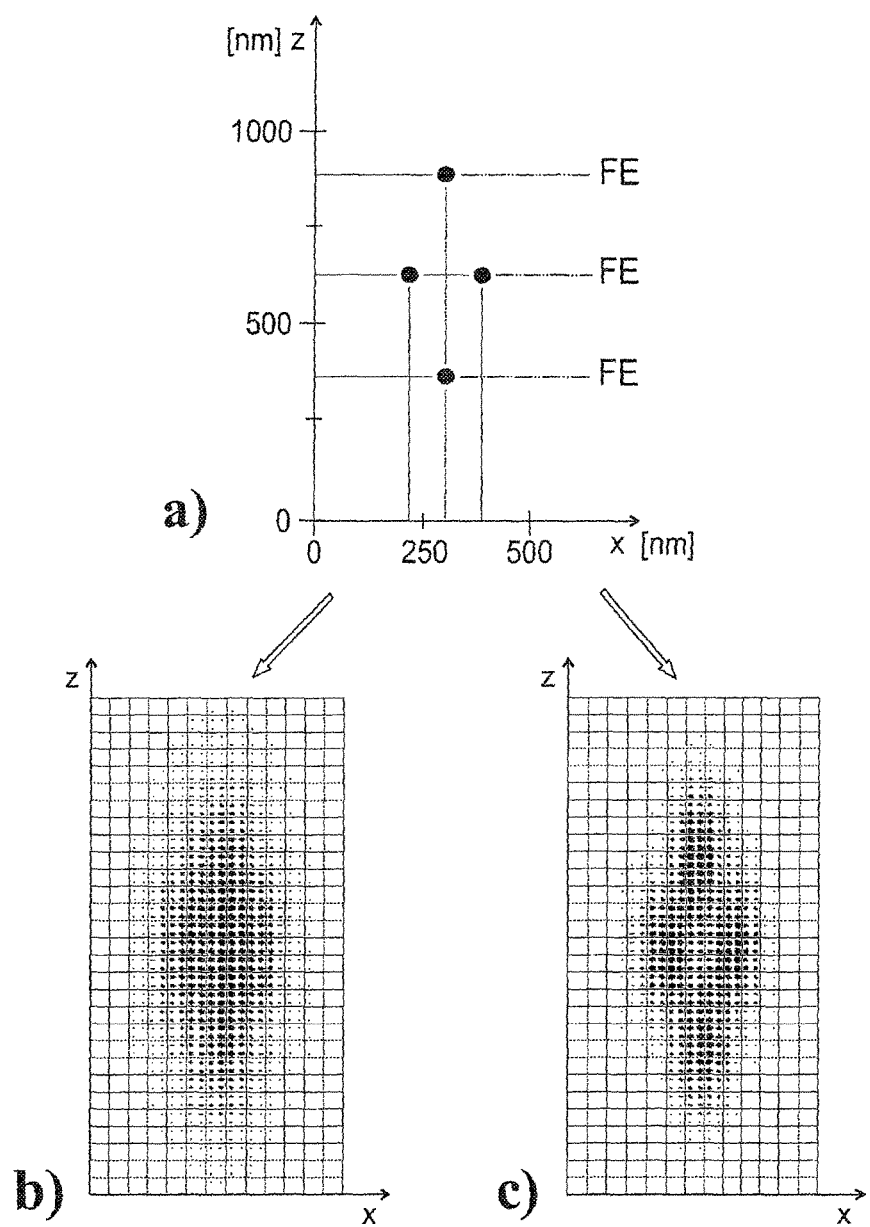
FIG. 4 shows the results of a simulation in which the fluorescence signals of an assumed structure of four points in the X-Z plane are traced back to the respective focal planes with the method according to the invention.

FIG. 4 shows the results of a simulation according to the method described referring to FIG. 1. It will be seen that the fluorescence signals 34 of an assumed structure with four points in the X-Z plane can be traced back to the corresponding focal planes FE with the method presented herein. Four stochastically fluctuating emitters whose position is shown in FIG. 4a as schematically spatial structure 52 in an X-Z plane of the sample 5 were simulated under simultaneous observation with fifteen Z planes (different focal planes FE). The simulated data comprise a time series of 100 frames, the triplet lifetime amounts to two frames. In FIG. 4b, the fluorescence signals 34 of all of the detector regions 31 are associated with their respective location in Z, but due to crosstalk of fluorescent light from blurrily imaged focal planes FE are superposed such that it is impossible to separate them for separating the fourfold structure 52. The right-hand diagram FIG. 4c shows the fluorescence signals 34 from a cross-correlation of the second order of the Z planes. The correlations are only formed between different Z planes but not in lateral direction. Accordingly, only the signals of diffraction orders BO of a scan point in the raster of the X-Z plane are correlated, and the fluorescence signals 34 of all of the detector regions 31 which are associated with two diffractions orders neighboring one another are used.

In the case shown in FIG. 4c, this results not only in the sought-after separation of fifteen Z planes but also in an increase in resolution in Z direction (also efficient intermediate pixels in Z). The positive effect of signal association on a presumably increased lateral resolution will also be noted: the two adjacent points of structure 52 can now be separated, not because the lateral resolving capacity of the microscope has increased, but because the fluorescence signal 34 of these two points is no longer superposed by the out-of-focus contributions of the other two points located one above the other. It is once more explicitly noted that the correlations at a respective X-Z scan point exclusively between different Z planes (i.e., diffraction orders BO on different detector regions) were included in the calculation. The method can be expanded such that (de-)correlations are evaluated in Z direction as well as in X direction and Y direction.

Figure 5B:
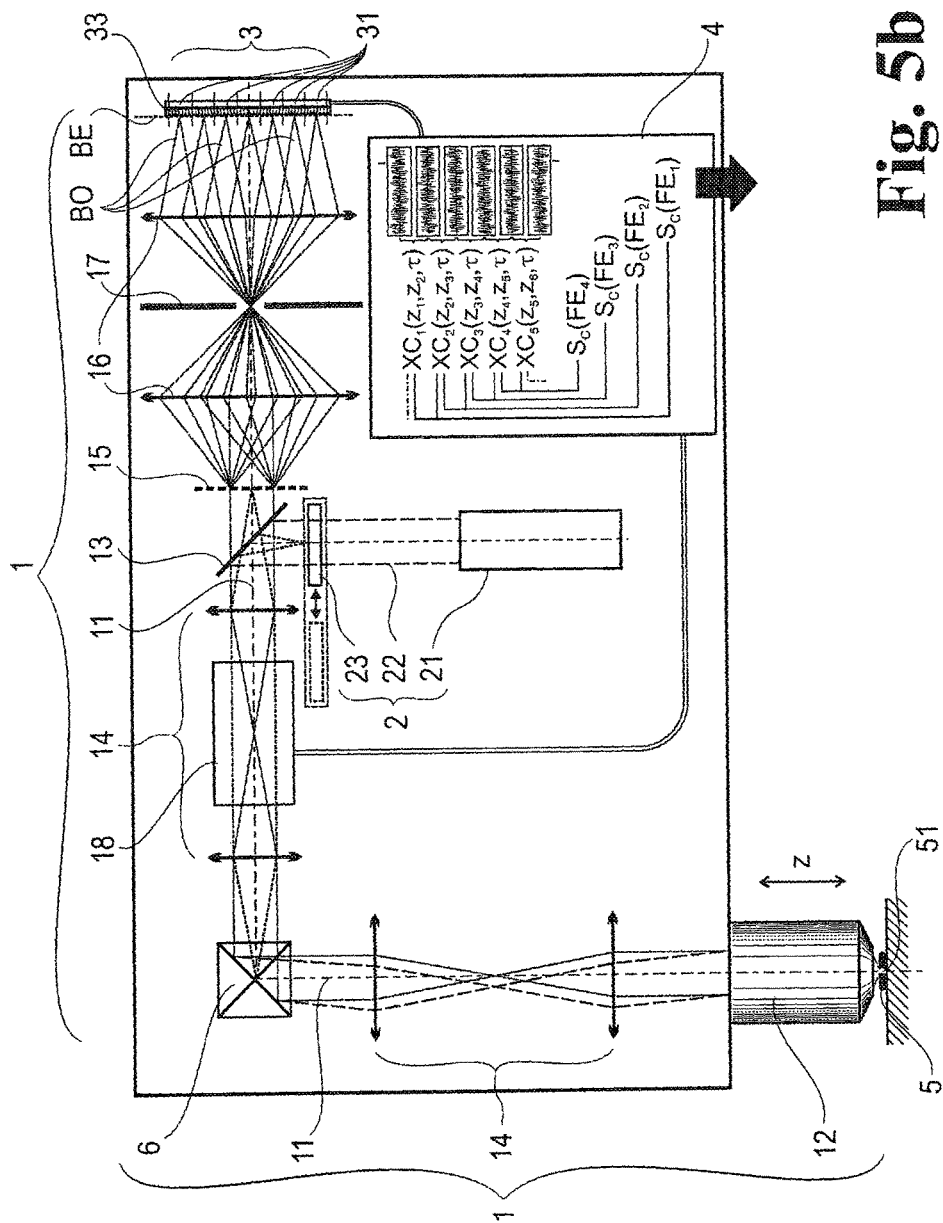

FIG. 5a and FIG. 5b show the method according to the invention realized in a typical LSM construction.

In this case, diffractive optics 15, e.g., in the form of an optical grating, for generating five different diffraction orders BO are assumed in FIG. 5a. To this end, an illumination system 2 with a laser 21 with simultaneous excitation and detection of fluorescence is directed to a sample 5 which has a thickness such that a depth scan in Z direction would be necessary for a normal CLSM (confocal LSM). The invention does not make use of this. In this case, the depth resolution (Z direction) is through excitation of fluorescence by means of an elongated PSF and a separation of the emitter locations.

Further, the illumination system 2 has a laser 21 for generating at least one illumination beam 22 which is coupled by a beam combiner 13 into a microscope observation beam path 1 which is defined by a measuring volume 51 of sample 5 to an image plane BE and comprises along an optical axis 11 a microscope objective 12, the beam combiner 13 and a detector unit 3 arranged in the image plane BE and makes possible the following sequence of steps in CLSM:

the illumination beam 22 is focused with the microscope objective 12 in the measuring volume 51, wherein the illumination beam 22 passes through a beam-forming phase mask 23 in an illumination pupil for generating an elongated focus, fluorescent light generated in the measuring volume 51 is collected and collimated by means of the microscope objective 12, and resulting light beams are routed to diffractive optics 15 arranged between the beam combiner 13 and the image plane BE, the light beams generated in the measuring volume 51 are split into beam bundles of different diffraction orders BO by means of the diffractive optics 15 and the different diffraction orders BO are imaged on separate detector regions 31 of the detector array 3 by means of detection optics 8, wherein the diffractive optics 15 impress upon the light beams of every diffraction order BO a spherical phase differing from the other diffraction orders BO so that fluorescent light from focal planes FE of different depths of the measuring volume 51 is associated with different diffraction orders BO and is deflected without confocal discrimination to the separate detector regions 31 by which fluorescent light from associated focal planes FE of the measuring volume 51 and fluorescence crosstalk from blurrily imaged adjacent focal planes FE of the measuring volume 51 are converted into electronic fluorescence signals 34, the fluorescence signals 34 which originate from different focal planes FE of the measuring volume 51 and on which crosstalk is superposed along the diffraction orders BO are associated with focal planes FE defined in the measuring volume 51 by means of correlation-based association of the fluorescence signals 34 based on distinguishable blinking behavior of fluorescing dyes in the measuring volume 51 so that an increased photo efficiency can be realized for every determined focal plane FE.

The aim of the method is not primarily to generate a superresolved image but rather, through subsequent pixel correlations, to make use of the separation and association of fluorescence signals of different fluorescing emitters, which are arranged in space (i.e., in the sample volume depth) and which are superposed multifocally in a multifocal LSM as a result of signal detection which is consciously not strictly confocally discriminated, for increasing photon efficiency. Therefore, this method may be referred to for the sake of brevity as CPI (correlated pixel imaging). The background to why this CPI approach works at all will be discussed in detail in the following paragraph.

Some time scales will now be considered for purposes of illustrating the parallelization of the evaluation of multiconfocal signals.

Fifty cycles (frames) for correlation analysis with a 1-μs frame time make it possible, for example, to acquire 25 pixel planes simultaneously in 50 μs and, correspondingly, a stack with 25*256*256* pixels in approximately three seconds.

This would correspond to 25 "normal" LSM scans of 0.12 seconds each, although an increased photon efficiency is achieved, or less power is required for the same SNR, in correlation-based multi-confocal fluorescence scanning microscopy.

Beyond this, however, this exemplary consideration still does not take into account the piezo adjusting times of about 100 ms per Z plane during the sequential measurement which are necessary according to "normal" LSM scans, which accordingly leads to an additional time gain of 2.5 s for the 25-fold frame stack with the multi-confocal detection according to the invention.

Therefore, the great advantage of the invention is that the depth measurement and the improved photon efficiency, particularly for showing dynamics in live-cell imaging, are concurrent.

Influencing the Lifetime of Dark States

The lifetime of triplet states and other dark states depends on many factors and can also be influenced by altering the chemical environment. In contrast to the known prior art (see, e.g., S. Geissbueher et al. (2011). "Comparison between SOFI and STORM"), Biomed. Opt. Express 2: 408-420, or Dertinger et al. (2010). "Superresolution optical fluctuation with organic dyes", Angewandte Chemie 122 (49): 9631-9633) in which the dark states are lengthened in order to shift the fluctuations into the timing detectable by cameras, it is even useful for the invention to shorten the fluctuations in order to keep the pixel dwell times as short as possible given sufficient correlation intervals. For one, this expands the application spectrum because—as was stated above—the triplet lifetimes of the most common dyes are within the range of several μs in any case. Beyond this, however, they can also be further shortened (cf. Zheng, Quinsi et al. (2012). "On the mechanisms of cyanine fluorophore photostabilization", The Journal of Physical Chemistry Letters 3 (16): 2200-2203). In this publication, it is shown, inter alia, that typical anti-fade reagents such as Trolox reduce the triplet lifetime of Cy5, for example, from ≈60 μs to 1 μs. This represents a double gain for the method according to the invention: first, the image capture time can be shortened and, second, the photobleaching can be even further reduced.

Adjustment of EDOF (Extended Depth of Focus) Versus Increased Resolution in Z

The proposed method has the potential of increasing the resolution in Z direction. However, the main objective here is the separation of the parallelly recorded Z planes. Nevertheless, the two effects can also be adjusted on demand. For example, a PSF with elongated focus (underfilled pupil or EDOF) can be adjusted with a given quantity of detector regions 31 at the expense of a real increase in resolution (for diffraction-limited imaging) in Z direction in order to increase the sample depth acquired simultaneously in a scan. The required spread of the focal plane splitting is achieved by means of zoom optics 18 between the scanner 6 and the diffractive optics 15 which are configured, for example, as chirped grating. Alternatively, the grating of the diffractive optics 15 can also be replaced. If two (different) relay optics 14 are used in conjunction with the scanner 6, the relay optics 14 which are arranged between the scanner 6 and the diffractive optics 15 can also take over the function of the zoom optics 18.

Increased Lateral Resolution

Depending upon the quantity and density of detector regions 31 or the size of a detector array 33 (pixel number), an increase in lateral resolution can also be carried out through fluctuation analysis (by fast detectors for each dye).

This property can be utilized in turn for optimizing a fast, sample-conserving 3D imaging. For example, if the aim is to acquire the largest possible Z region in parallel, an illumination PSF which is as "long" as possible would be selected. If the latter is realized by underfilling the objective pupil, this results in a reduction in lateral resolution. However, through the lateral correlation of the signals, a resolution can be counted on which would correspond to a smaller focus.

Combining the Method with Numerical Deconvolution

As was described above, the method according to the invention leads inherently to a kind of deconvolution. Of course, a reworking of the data with one of the known methods is also conceivable. The data for a numerical deconvolution can advantageously be generated precisely because planes neighboring one another in Z direction are captured with the method according to the invention. Further, measuring a plurality of lateral pixels per focal plane FE through the use of a deconvolution offers the possibility of dispensing with the step of decorrelation and deconvolving the data directly with a (possibly previously measured) PSF. In order to make optimal use of the method, the overall optical system of the observation beam path 1 should be configured correspondingly. Suitable detection optics 16 arranged downstream of the diffractive optics 15 are configured such that they focus all of the split diffraction orders BO into the opening of a confocal aperture 17 (shown only in FIG. 5b) located in front of the receiver in conventional CLSM. This confocal aperture 17 is wide open for the method according to the invention. Accordingly, all of the beam bundles of the various diffraction orders BO are deflected to detector regions 31 which are arranged at a distance behind the aperture such that the beam bundles diverge at least by a distance corresponding to the spacing between the individual detector regions 31 until they impinge on the detector unit 3. Alternatively, detector regions 31 can be arranged in a further conjugate image plane.

Separation of Dyes Based on Decorrelation Times

Since decorrelation times are dye-specific, the emitter species can also be deduced from the fluorescence blinking statistics. Accordingly, multi-channel images would be possible with a detector and without color splitting in the detection path, or the two methods could possibly be combined (conventional color separation via filters and additional color separation over decorrelation times). Accordingly, the quantity of dyes which are used and which are to be measured simultaneously can be increased by means of corresponding combinatorics. For example, dyes with overlapping emission spectra could be used simultaneously if their decorrelation times were appreciably different. This allows a further parallelization of the fluorescence evaluation which can now be utilized for spectral analysis.

Similar to the separation of dyes based on their spectral characteristics, there exists the possibility of crosstalk between the color channels. This is not caused by an overlapping of emission spectra, but rather by the overlapping of confidence intervals.

Apparatus for Carrying Out the Method

The beam path of a multi-confocal LSM is shown schematically in FIG. 5. Laser light is guided along the illumination beam path 2 so as to be collimated by the laser 21 and is deflected in direction of the sample 5 at the beam combiner 13 which can be configured as a dichroic beamsplitter. The scanner 6 (preferably galvanometer or MEMS) scans an illumination beam 22 of the laser 21 laterally over the sample 5. The microscope objective 12 generates the illumination focus which images the objective pupil in the plane of the scanning mirror of the scanner 6 or in the detection pupil or illumination pupil via the relay optics 14 arranged before and after the scanner 6 in the observation beam path 1. A phase mask 23 which produces an elongated focus in the depth dimension (Z direction) of the sample is inserted in the illumination pupil. The phase mask 23 can be a cubic phase mask. Alternatively, a ring diaphragm can also be inserted for generating a Bessel beam or other non-diffractive beam (sometimes referred to as self-reconstructing beam).

Further, instead of the phase mask 23, the beam radius can be adjustable through zoom optics 18 in the illumination beam 2 such that an elongated focus is generated by underfilling the pupil of the microscope objective 12. The fluorescence generated along the focus is collected through the microscope objective 12 and runs through the observation beam path 1 in the opposite direction. The fluorescent radiation is transmitted through dichroic beam splitting in the beam combiner 13. A two-dimensional chirped grating which impresses a constant defocus on each diffraction order BO is inserted in the detection pupil as diffractive optics 15. The detection optics 16 image each diffraction order BO on an own detection region 31 of the detector array 33. Accordingly, a different focal plane FE in the measuring volume 51 of the sample 5 is associated with each detector region 31 and is sharply imaged on the detector regions 31 in the image plane BE.

The distance between the focal planes FE under consideration is adjustable through the zoom optics 18 and is controlled by the evaluating and controlling unit 4. The signal data are transmitted from the detector array 33 into the evaluating and controlling unit 4, where they are evaluated for each correlation analysis and/or 3D convolution according to the above description. In doing so, the defocused signal components are associated with their origin plane in the measuring volume 51 based on their correlated blinking behavior. The consequent nonoccurrence of the cutting out of signal components defocused through confocal discrimination results in the increased photon efficiency in accordance with the invention.

Insofar as the method according to the invention is implemented with a conventional confocal scanning microscope (CLSM) as is shown in FIG. 5b, a detector aperture 17 constituting the confocal discriminator as pinhole in a CLSM is provided downstream of the beam combiner 13 constructed as color splitter in direction of the detector 3. In this case, however, this detector aperture 17 which is arranged in an intermediate image plane between two detector optics 16 configured as relay optics serves—in a wide open condition—merely for rough scatter light discrimination.

The sensitivity of a measuring apparatus in the form of the CLSM, shown in FIG. 5b, depends not only on the brightnesses of the dyes that are used but also on the speed of the lateral scan which—owing to the temporal behavior of the blinking statistics (ON/OFF time scale) of the dyes—should be a function of the decorrelation times of the dye under consideration.

Figure 6:
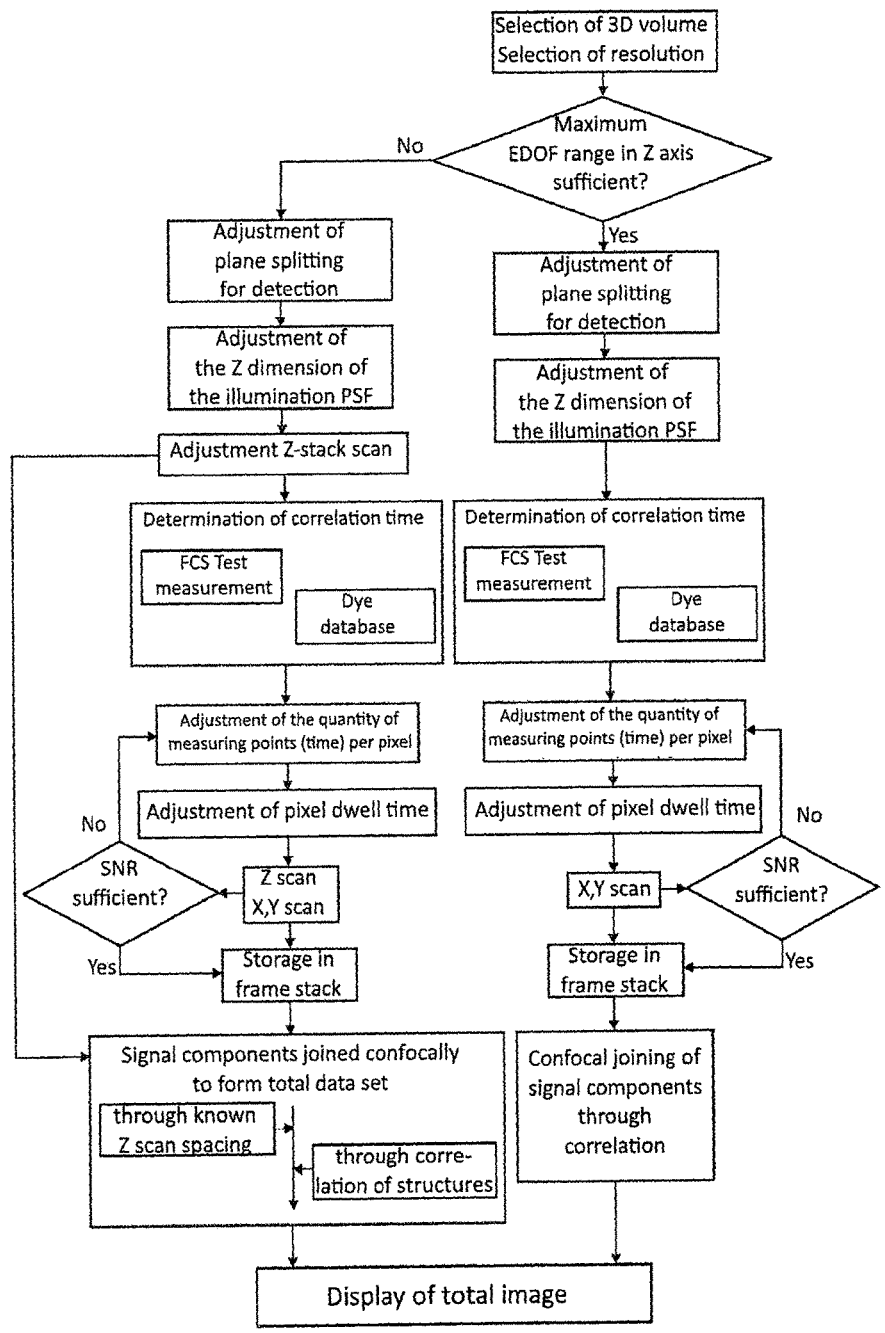
FIG. 6 is a flow chart for optimal EDOF adjustment over the scan organization to the correlation analysis with weighting for generating a complete frame stack of correlation signals as equivalent 3D display of an intensity structure detected in the sample.

Therefore, it may be advantageous to adjust the speed of the scan adaptively during the image capture as will be seen from the flow chart in FIG. 6. The speed of the X,Y scanner 6 is adjusted to the sample 5 depending on the quality of the recorded data. The triplet lifetime (or, broadly speaking, the characteristic blinking time) of the dye system determines the speed. With longer triplet times and/or poor SNR, scanning would have to be carried out more slowly to acquire a sufficient number of correlation cycles through longer pixel dwell times. The following considerations are crucial in this regard.

First Evaluation:

For a triplet time $\tau=3$ µs, 50 measuring points of the blinking time as necessary quantity of "correlation points" are acquired during a pixel dwell time of 150 µs. However, if the triplet time amounts to $\tau=10$ µs, a pixel dwell time of 500 µs is required for the same 50 measuring points.

Second Evaluation:

The quality of a correlation signal of 10 measuring points is not sufficient for a reliable correlation of the fluorescence signals 34 of the detector regions 38; at least 20 measuring points of the triplet blinking are required. Therefore, the speed of the scanner 6 must be reduced; that is, the X, Y scan can be carried out only half as quickly.

To adjust the scanning speed, an FCS measurement is advisably taken at a spot either before the image capture or together with the imaging of a small area for determining the parameters for a stack of frames. This test measurement can likewise be seen from the flow chart in FIG. 6.

A possibility for separate adjustment of illumination PSF length and detection plane Z spacing is useful for flexible adjustment of Z resolution relative to the spread of the planes of the parallelized Z scanning.

The following adjustment parameters and adjustment alternatives apply to illumination beam 22:

single-photon excitation or multiphoton excitation,

Gaussian profile, underfilling of pupil (adjustable through beam-forming element, e.g., phase mask 23 or mask for amplitude apodization (also possible with changing device) in front of the beam combiner 13 (usually main color splitters in a commercial CLSM);

generation of a EDOF PSF by means of a Bessel beam (or comparably acting non-diffractive beam), DOF adjustable through adaptive optics (e.g., zoom optics 18 or relay optics 14) after the beam combiner 13; and adjustment of the laser intensities for an optimal blinking behavior (in some cases, the blinking is heavily dependent upon the intensity).

The multi-spot splitting in Z direction can be positively influenced in the following ways.

By means of optics arranged outside of the observation beam path 1 in front of the beam combiner input for coupling the illumination system 2, only the dimension of the illumination volume, i.e., the (object-side) focal depth (focal dimension) of the microscope objective 12 is lengthened, but the measuring volume 51 at various points of the illumination volume is not affected. While the axial resolving capacity is reduced in this way, more measuring volumes are excited simultaneously with identical light output by the focal depth (EDOF or elongated depth of field) of the illumination volume expanded in this way.

The optics for generating an expanded focal depth comprise a phase plate 23, particularly a cubic phase modulation mask, or means for generating Bessel beams arranged, respectively, in a plane conjugate to the pupil plane of the microscope objective, or are configured for underfilling the pupil of the microscope objective, particularly through beamforming for reducing a beam cross section of collimated light. Cubic phase modulation masks for generating an expanded focal depth are described, for example, in Dowski/Cathey, "Extended depth of field through wave-front coding", *Applied Optics* 34 (11): 1859. Optics for underfilling the pupil can be, for example, a beamformer reducing the beam cross section in the pupil. The underfilling of the pupil leads to a reduction in the numerical aperture of the illumination resulting in a poor axial resolving capacity ΔZ.

In order to generate an axially lengthened illumination volume, any other known EDOF-type optics can also be used to generate Bessel beams as described in Y. Lin, "Experimental investigation of Bessel beam characteristics" Applied Optics 31: 2708, or impressing a cubic phase characteristic on the illumination light as also described in Applied Optics 34 (11): 1859. Further, a light source or optics arranged downstream of the light source which axially define a point series corresponding to the measuring volumes 51 as is described, for example, in DE 103 56 416 A1 with reference numeral 11 can also be advantageous. The advantage consists in the improved resolution in every axial focal plane FE because, in this case, complete confocality can be achieved (the disadvantage consists in an expanded illumination of the sample 5 with correspondingly higher stress).

The zoom optics 18 for expanding the focal depth (elongated focus) generate an illumination volume whose axial dimension is at least four times, particularly more than ten times, preferably at least twenty times, its lateral dimension and/or corresponds to at least two optical section thicknesses of the microscope for a predetermined excitation wavelength, a predetermined numerical aperture of the microscope objective 12, a predetermined confocal aperture size and a predetermined refractive index of an immersion medium. Accordingly, the diffractive optics 15 can be configured to provide a sufficient axial distance for optical separation compared to the prior art.

The optical element for the beamforming of illumination (phase plate 23 or diffractive optics 15) is preferably configured such that middle points of neighboring axial measuring volumes 51 for a predetermined excitation wavelength, a predetermined numerical aperture of the microscope objective 12, a predetermined size of the confocal aperture 17 and a predetermined refractive index of an immersion medium are separated from one another by more than two optical section thicknesses of the LSM. However, a required axial separation of the measuring volumes 51 through adjustment of the axial splitting by means of grating parameters of the diffractive optics 15 can be achieved by corresponding configuration of the diffractive element in a given microscope objective 12.

The optics for increasing the elongated focus are advantageously configured in such a way that all measuring volumes 51 imaged in the image plane BE lie within the elongated focus, that is, when the illumination system 2 with elongated focus (EDOF) in the sample 5 is adapted to the areas (measuring volumes 51) covered by the detection means. In this way, the excitation light of the illumination beam 22 can be efficiently utilized so as to conserve the sample 5. To this end, with a given grating of the diffractive optics 15 in the detection beam path, the illumination optics (zoom optics 18 or phase mask 23) in the illumination beam path 2 can be adapted such that the measuring volumes 51 are completely illuminated, or, with a given light distribution in the sample 5 in the detection beam path, the diffractive optics 15 can be adapted such that the illuminated areas are completely imaged (and detected).

For image reconstruction, there are the following options.

Image reconstruction is carried out via a lateral scanning (optionally also in conjunction with an additional mechanical Z scan, wherein by means of the multi-(con)focal Z scan—in contrast to classical LSM—in the method according to the invention with a lateral scan (X, Y) a 3D sample volume is already imaged and only the "Z capture range" can be additionally increased if even more expanded measuring volumes 51 of the sample 5 need to be imaged.

Use of scanning technologies such as galvanometer scanner, MEMS scanner, acousto-optical lens (AOL), acousto-optical modulator (AOM), EO scanner, etc.).

For detection, there are the following variants for adjustment and control.

The conventional CLSM pinhole (as detector aperture 17) can be used with the following operating modes:
small pinhole (switchable with diameter 0 . . . 10 AU) for conventional standard confocal detection as standard CLSM;
large pinhole 17 for optimal detection when using the described invention; or
no pinhole for somewhat inferior application of the invention due to scatter light.

The diffractive optics 15 can be configured as follows:
in the form of a decentered individual diffractive optical element (individual DOE);
in the form of a DOE changer;
fixed DOE with upstream magnification optics (zoom optics 18 or optics changer).

A spectral recording can be realized (e.g., in order to take into account different blinking cycles in the dyes in that the longest blinking time determines the "pixel dwell time", wherein the separation of the blinking cycles is typically carried out by means of spectral filters.

The following sensor arrays can be used in the detector unit 3:
SPAD array (Single Photon Avalanche Diode array);
PMT array (Photo-Multiplier Tube array) with/without means for redistributing the intensity distribution on the sensor geometry, e.g., fibers, FOPS, CMOS camera;
CMOS camera with image amplifier (e.g., multi-channel plate or micro-channel plate);
EMCCD (Electron-Multiplying CCD) with low pixel number for high readout rate; and
sCMOS camera.

In the many possible variations mentioned above, the necessary precondition for implementing the method according to the invention is the multi-confocal operating mode of a CLSM with beam splitting by means of DOEs, as described above, combined with a numerical analysis/computation of data by means of which the defocused signals are assigned to their origin plane in that the signal data are processed with a numerical method of a correlation analysis (e.g., second-order cross-correlation) or a 3D deconvolution.

To this end, FIG. 6 shows a flow chart in which the above-mentioned adjustment possibilities are taken into account. In particular the different adaptation of the increased depth resolutions of the focal planes FE alternates with the adjustment of the required depth range of the mechanical-optical Z scan through the adjustment steps of the plane splitting for detection, the Z dimension of the illumination PSF and the mechanical/optical Z scan. A further mutual adjustment option is the determination of the correlation time in which an optimum is sought between possible dyes, the results of an FCS test measurement and the real blinking times of the dye in order to adjust the required pixel dwell time so that a sufficient frame cycle is available for the correlation.

There exists the further possibility of optimizing the X-Y scan (possibly in addition to the Z scan) in order to obtain an adequate signal-to-noise ratio (SNR) before the correlated allocation of signal components associated with the individual focal planes FE (and intermediate planes, if any) and storage or display in ordered stacks of stored frames as confocal 3D result image.

The method can be carried out for further parallelization and, therefore, a further increase in sample throughput with a plurality of beam bundles for additional lateral parallelization. The use of multiple beams offers the advantage that it allows a more comprehensive adaptation to the blinking statistics of the dyes at a given frame rate.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

LIST OF REFERENCE CHARACTERS 1 observation beam path
11 optical axis
12 microscope objective
13 beam combiner
14 relay optics
15 diffractive optics
16 detection optics
17 detector aperture (pinhole)
18 zoom objective
2 illumination system
21 laser
22 illumination beam
23 phase mask
3 detector unit
31 detector region
32 individual detector
33 detector array
34 (electronic) fluorescence signals
4 evaluating and controlling unit
41 allocation unit
42 cross-correlator
5 sample
51 measuring volume
6 scanner
BE image plane
BO diffraction order
FE focal plane

What is claimed is:

1. Method for evaluating signals of fluorescence scanning microscopy with simultaneous excitation and detection of fluorescence in different focal planes of a sample by means of confocal laser scanning microscopy, comprising:
coupling at least one illumination beam by means of a beam combiner into a microscope observation beam path which is defined by a measuring volume of the sample up to an image plane and which has, along an optical axis, a microscope objective, the beam combiner and a detector unit arranged in the image plane;
focusing the illumination beam with the microscope objective in the measuring volume, wherein the illumination beam passes through a beam-forming phase mask in an illumination pupil for generating an elongated focus;
collecting and collimating fluorescent light generated in the measuring volume by means of the microscope objective, and routing resulting light beams to diffractive optics arranged between the beam combiner and the image plane;
splitting the light beams generated in the measuring volume into beam bundles of different diffraction orders by means of the diffractive optics, and imaging the different diffraction orders on separate detector regions of the detector array by means of detection optics, wherein the diffractive optics impress upon the light beams of every diffraction order a spherical phase differing from the other diffraction orders so that fluorescent light from focal planes of different depths of the measuring volume is associated with different diffraction orders and is deflected without confocal discrimination to the separate detector regions by which fluorescent light from associated focal planes of the measuring volume and fluorescence crosstalk from blurrily imaged adjacent focal planes of the measuring volume are converted into electronic fluorescence signals; and
associating the fluorescence signals which originate from different focal planes of the measuring volume and on which crosstalk is superposed along the diffraction orders with focal planes defined in the measuring volume by means of correlation-based association of the fluorescence signals based on distinguishable blinking behavior of fluorescing dyes in the measuring volume.

2. Method according to claim 1, wherein said association of the fluorescence signals with the focal planes is carried out through second-order cross-correlation of signal sequences of two detector regions of neighboring diffraction orders.

3. Method according to claim 2, wherein the cross-correlation of the signal sequences is carried out over a time period adapted to the fluorescence blinking of the dyes.

4. Method according to claim 3, further comprising using dyes with a duration of an OFF state of fluorescence blinking between 0.1 µs and 500 µs, preferably between 5 and 50 µm.

5. Method according to claim 3, wherein the correlation of signal sequences is carried out over a quantity of frames corresponding to ten times to one thousand times an OFF state of the fluorescence blinking.

6. Method according to claim 5, wherein the correlation of signal sequences is carried out over a quantity of frames twenty to fifty times the OFF state of the fluorescence blinking.

7. Method according to claim 2, further comprising carrying out a 3D deconvolution in addition to the cross-correlation.

8. Method according to claim 1, further comprising illuminating the measuring volume with elongated focus in order to further spread out a given quantity of focal planes in the measuring volume depth.

9. Method according to claim 8, wherein the spreading out of the focal planes and an increased resolution in the measuring volume depth can be selectively adjusted in that the elongated focus is adjusted by means of a zoom objective between the sample and the diffractive optics.

10. Method according to claim 8, further comprising adjusting the elongated focus by underfilling the entrance pupil of the microscope objective.

11. Method according to claim 10, wherein an additional correlation of fluorescence signals scanned in lateral planes of the sample with increased lateral resolution is achieved to supplement the correlation of fluorescence signals in depth with elongated focus which is expanded by underfilling the entrance pupil of the microscope objective.

12. Method according to claim 1, further comprising carrying out an additional correlation in addition to the correlation in depth, for fluorescence signals scanned in lateral planes of the sample.

13. A confocal fluorescence scanning microscope with an optical system which defines a microscope observation beam path from a measuring volume to an image plane having a microscope objective, a beam combiner for coupling an illumination system, and an aperture arranged in the image plane, comprising
- diffractive optics in the observation beam path of the optical system between the beam combiner and the image plane for splitting light beams into beam bundles along different diffraction orders, wherein there is impressed on the beam bundles of every diffraction order a spherical phase which differs from the other diffraction orders, and detection optics for focusing the split beam bundles on separate detector regions of the detector array,
- said detector array having a number of separately readable detector regions which corresponds to the quantity of diffraction orders so that fluorescent light arriving from a defined focal plane in the associated diffraction order and crosstalk fluorescent light from neighboring focal planes in the same diffraction order can be received in the detector regions, and
- on evaluating and controlling unit arranged downstream of the outputs of the detector regions associating the fluorescence signals which originate from the same focal planes but which are received by different detector regions, which evaluating and controlling unit comprises means for correlating different signal components and for associating correlating signal components with exactly one focal plane in each instance based on distinguishable blinking behavior of fluorescing dyes in the measuring volume.

14. The confocal fluorescence microscope according to claim 13, wherein said diffractive optics are configured as a chirped grating.

15. The confocal fluorescence microscope according to claim 13, wherein said diffractive optics impresses a spherical phase upon the light beams of every diffraction order, which spherical phase differs from the other diffraction orders by an integral multiple in each instance.

16. The confocal fluorescence microscope according to claim 13, further comprising zoom optics forming an elongated focus for underfilling the entrance pupil of the microscope objective.

17. The confocal fluorescence microscope according to claim 13, wherein said laser for exciting the sample generates a Bessel beam or other non-diffractive beam forming an elongated focus.

18. The confocal fluorescence microscope according to claim 16, characterized in that said zoom optics for underfilling the entrance pupil of the microscope objective spreads apart the distances of the focal planes.

19. The confocal fluorescence microscope according to claim 13, further comprising means for lateral scanning and linking means for generating a stack of laterally two-dimensionally scanned frames in different focal planes comprising fluorescence signals which are captured pixel by pixel and by cross-correlation of signal components associated with the various focal planes.

20. The confocal fluorescence microscope according to claim 19, further comprising a cross-correlator in the evaluating and controlling unit associating signal components with exactly one focal plane for analyzing fluorescence signals from respective vertically adjacent focal planes and laterally adjacent pixels of the frames.

21. The confocal fluorescence microscope according to claim 19, further comprising a processor unit in the evaluating and controlling unit for associating signal components with exactly one focal plane, for 3D deconvolution of fluorescence signals from respective vertically adjacent focal planes and laterally adjacent pixels of the frames.

* * * * *